United States Patent [19]
Tyan et al.

[11] Patent Number: 5,998,485
[45] Date of Patent: Dec. 7, 1999

[54] METHOD FOR MODULATING IMMUNE RESPONSE WITH INOSITOL

[75] Inventors: Marvin L. Tyan; Dolly B. Tyan, both of Los Angeles, Calif.

[73] Assignee: Cedars-Sinai Medical Center, Los Angeles, Calif.

[21] Appl. No.: 08/874,470

[22] Filed: Jun. 16, 1997

[51] Int. Cl.$^6$ .................................................. A61K 31/045
[52] U.S. Cl. .......................... 514/724; 514/728; 514/103
[58] Field of Search ................................... 514/103, 724, 514/728

[56] References Cited

U.S. PATENT DOCUMENTS

| | | | |
|---|---|---|---|
| 5,051,411 | 9/1991 | Siren | 514/103 |
| 5,082,833 | 1/1992 | Shamsuddin | 514/143 |
| 5,342,832 | 8/1994 | Siren | 514/103 |

FOREIGN PATENT DOCUMENTS

| | | |
|---|---|---|
| 0 508 488 A2 | 4/1987 | European Pat. Off. . |
| 0 359 259 A2 | 9/1989 | European Pat. Off. . |
| WO 92/11867 | 7/1992 | WIPO . |

OTHER PUBLICATIONS

Asplin, et al. "chiro–Inositol deficiency and insulin resistance: A comparison of the chiro–inositol–and the myo–inositol–containing insulin mediators isolated from urine, hemodialysate, and muscle of control and type II diabetic subjects," *Proc. Natl. Acad. Sci. USA*, 90:5924–5928 (Jul. 1993).

Atack, et al., "Characterization of the effects of lithium on phosphatidylinositol (PI) cycle activity in human muscarinic m1 receptor–transfected CHO cells," *Brit J.. Pharmacology*, 110:809–815 (1993).

Baten, et al., "Inositol–phosphate–induced enhancement of natural killer cell activity correlates with tumor suppression," *Carcinogenesis*, 10(9):1595–1598 (1989).

Bento, et al., "Glycoinositolphospholipids Purified from *Trypanosoma cruzi* Stimulate lg Production In Vitro," *J. Immunol.*, 157:4996–5001 (1996).

Berridge, Michael J., "Inositol trisphosphate and calcium signalling," *Nature*, 361:315–325 (Jan. 1993).

Berridge, Michael J., "Inositol Trisphosphate and Diacylglycerol: Two Interacting Second Messengers," *Ann. Rev. Biochem*, 56:159–193 (1987).

Bruzik, et al., "Are–D–and L–chiro–Phosphoinositides Substrates of Phosphatidylinositol–Specific Phospholipase C?," *Biochemistry*, 33:8367–8374 (1994).

Galasko, et al., "Circulating Factors and Insulin Resistance. I.A. Novel Myoinositol 1,2–Cyclic Phosphate Phosphoglycan Insulin Antagonist from Human Plasma Is Elevated in Noninsulin–Dependent Diabetes Mellitus," *Jour. Clin. Endocrinology and Metabolism*, 80(5):2419–2429 (1995).

Hallman, et al., "Inositol Supplementation in Premature Infants with Respiratory Distress Syndrome," *N. Engl. J. Med.*, 326(19):1233–1239 (1992).

Hansbro, et al., "Kinetic Analysis of Novel Inhibitors of Inositol Polyphosphate Metabolism," *Biochemical and Biophyical Research Comm.*,200(1):8–15 (Apr. 15, 1994).

Huang, et al., Chiroinositol Deficiency and Insulin Resistance. III. Acute Glycogenic and Hypoglycemic Effects of Two Inositol Phosphoglycan Insulin Mediators in Normal and Streptozotocin–Diabetic Rats in Vivo, *Endocrinology*, 132(2):652–657 (1993).

Johnson, et al., "Synthesis and Evaluation of 3–Modified 1D–myo–Inositols as Inhibitors and Substrates of Phosphatidylinositol Synthase and Inhibitors of myo–Inositol Uptake by Cells," *J. Med. Chem.*, 36:3628–3635 (1993).

Johnson, et al., "Synthesis of the 3–deoxy–3–C–(phosphonomethyl) analogue of 1D–myo–inositol 3–(dihydrogenphosphate)," *Carbohydrate Research*, 250:315–321 (1993).

Kofman, et al., "Myo–inositol attenuates the enhancement of the serotonin syndrome by lithium," *Psychopharmacology*, 118:213–218 (1995).

Mason, et al.,, "A neurophysiological study of a lithium–sensitive phosphoinositide system in the hamster suprachiasmatic (SCN) biological clock in vitro," *Neuroscience Letters*, 144:135–138 (1992).

Morris, et al., "Phosphatidylinositol Phospholipase C Is Activated Allosterically by the Aminoglycoside G418," *Journal of Bio. Chem*, 271(26)15468–15477 (Jun. 28, 1996).

Ortmeyer, et al., "Chiroinositol Deficiency and Insulin Resistance. I. Urinary Excretion Rate of Chiroinositol Is Directly Associated with Insulin Resistance in Spontaneously Diabetic Rhesus Monkeys," *Endocrinology*, 132(2):640–645 (1993).

Ortmeyer, et al., "Chiroinositol Deficiency and Insulin Resistance. II. Acute Effects of D–Chiroinositol Administration in Streptozotocin–Diabetic Rats, Normal Rats Given a Glucose Load, and Spontaneously Insulin–Resistant Rhesus Monkeys," *Endocrinology*, 132(2):646–651 (1993).

Ostlund, Jr., et al., "D–chiro–Inositol metabolism in diabetes mellitus," *Proc. Natl. Acad. Sci. USA*, 90:9988–9992 (Nov. 1993).

(List continued on next page.)

*Primary Examiner*—Theodore J. Criares
*Attorney, Agent, or Firm*—Viviana Amzel; Pretty, Schroeder & Poplawski

[57] ABSTRACT

A composition for modulating immune response in mammals, comprises a therapeutic agent such as a stereoisomer of inositol, derivatives, salts, and mixtures thereof, and optionally a carrier. The composition is provided in solid and liquid formulations, including solutions, suspensions, spreadable and solid forms, as an implant, inhalant, and in vaporizable, injectable, oral and transdermal forms, and the like. The composition of the invention is useful for modulating (enhancing/inhibiting) the immune response. The therapeutic agent of this invention enhances/suppresses B and/or T lymphocyte activity(ies) in normal, aging and immunodeficient mammals, as well as those afflicted with auto-immune disease (s), or subjected to transplants.

56 Claims, 2 Drawing Sheets

OTHER PUBLICATIONS

Ostlund, Jr., et al., "A Stereospecific myo–Inositol/D–chiro–Inositol Transporter in HepG2 Liver Cells," *Journal of Biological Chemistry,* 271(17):10073–10078 (Apr. 26, 1996).

Pak, et al., "Insulin stimulates the biosynthesis of chiro–i-nositol–containing phospholipids in a rat fibroblast line expressing the human insulin receptor," *Proc. Natl. Acad. Sci. USA,* 90:7759–7763 (Aug. 1993).

Raffa, et al., "Morphine antinociception is mediated through a LiCl–sensitive, $IP_3$–restorable pathway," *European Jour. of Pharmacology,* 215:357–358 (1992).

Raffa, et al., "Opioid efficacy is linked to the LiCl–sensitive, inositol–1,4,5–trisphosphate–restorable pathway," *European Jour. of Pharmacology,* 217:221–223 (1992).

Shamsuddin, et al., "Inositol and inositol hexaphospnate suppress cell proliferation and tumor formation in CD–1 mice," *Carcinogenesis,* 10(8):1461–1463 (1989).

Suzuki, et al., "Urinary chrio–Inositol Excretion is an Index Marker of Insulin Sensitivity in Japanese Type II Diabetes," *Diabetes Care,* 17(12):1465–1468 (Dec. 1994).

Tagliaferri, et al., "1L–2,3:4,5–Bis–O–(tetraisopropyldisi-loxane–1,3–diyl)–chiro–inositol: a useful intermediate for the preparation of several novel cyclitols," *Carbohydrate Research,* 266:301–307 (1995).

Tyan, Marvin L., "Inhibition of in Vitro Immune Responses by Antisera to H–2 or Ir Gene Products," *Proceedings of the Society for Exper. Bio. and Med.,* 150:313–317 (1975).

Weetman, et al., "The Enhancement of Immunoglobulin Synthesis by Human Lymphocytes with Lithium," *Clinical Immunology and Immunopathology,* 22:400–407 (1982).

Weiss, A., et al., "The Role of T3 Surface Molecules in the Activation of Human T Cells: A Two–Stimulus Requirement for IL 2 Production Reflects Events Occurring at a Pre–Translational Level", *J. Immunol.,* 133(1): 123–127, (1984).

Duke, R.C., et al., "Cytotoxic Lymphocyte–Derived Lytic Granules Do Not Induce DNA Fragmentation In Target Cells", *J. Immunol.,* 141(7): 2191–2194, (1988).

Devos, R., et al., "Induction of Cytolytic Cells by Pure Recombinant Human Interleukin 2", *Verlag Chemie GmbH.D.–40 Weinheim,* pp. 1057–1060. (1980).

Berkower, I., et al., "T Cell Clones to Two Major T Cell Epitopes of Myoglobin: Effect of I–A/I–E Restriction on Epitope Dominance", *J. Immunol.,* 135(4): 2628–2634, (1985).

Schmid, D.S., "The Human MHC–Restricted Cellular Response to Herpes Simplex Virus Type 1 is Mediated by $CD4^+$, $CD8^-$ T Cells and is Restricted to the DR Region of the MHC Complex", *J. Immunol.,* 140(10): 3610–3616, (1988).

Jacobson, S., et al., "Measles Virus–Specific $T4^+$ Human Cytotoxic T Cell Clones are Restricted by Class II HLA Antigens", *J. Immunol.,* 133(2): 754–757, (1984).

Golstein, P., "Sensitivity of Cytotoxic T cells to T–Cell Mediated Cytotoxicity", *Nature,* 252: 81–83, (1974).

Marrack, P., et al., "The Development of Helpter T Cell Precursors in Mouse Thymus", *J. Immunol.,* 140(8): 2508–2514, (1988).

Urban, J.L., et al., "Restricted Use of T Cell Receptor V Genes in Murine Autoimmune Encephalomyelitis Raises Possibilities for Antibody Therapy", *Cell,* 54: 577–592, (1988).

Pacific Basin Gathering in Hawaii Fills with Chemists, Meeting Briefs *Science,* vol. 271:145–146, (1996).

Wilcox, A., et al. "Modification at C2 of Myo–Inositol, 1,4,5–Triphosphate Produces Inositol Phosphates and Tetrakisphosphates with Potent Biological Activites", *Biochem.* 223: 115–124 (1994).

Downes, C.P., et al. "Studies of Inositol Analogues as Inhibitors of the Phosphoinositide Pathway, and Incorporation of 2–Deoxy–2–Fluoro–Myo–Inositol to Live Analogues of Phosphatidylinositol Intermediates", *Chem. J.,* 277: 407–412, (1991).

Lampe, D., et al., "Synthesis of Selective Non–$ca^{2+}$–Mobilizing Inhibitors of D–myo–Inositol 1,4,5–Trisphosphate 5–Phosphatase", *J. Med. Chem.,* 37:907–912, (1994).

METHOD FOR MODULATING IMMUNE RESPONSE WITH INOSITOL

This work was partially supported by the United States Department of Veterans Affairs. The United States Government may have rights in this invention.

BACKGROUND OF THE INVENTION

1. Field of the Invention

The present invention relates to methods and compositions for modulating immune response in a mammal.

2. Description of the Background

An immune response to an antigenic agent, be it a foreign antigen or an auto-antigen, is generally characterized by the production of antibodies by B lymphocytes and/or by destruction by T lymphocytes and/or natural killer (NK) cells of any cells displaying those antigens. Defects in B and/or T lymphoid cells, however, may result in the development of immunodeficiency diseases and/or the impairment of immune response function. The immune deficiency or defect may be congenital, caused by a mutation in a gene, or it may be acquired, for example, through a viral infection or as a result of the aging process. The thus produced defect may or may not be fatal, depending on the stage of stem cell or lymphocyte differentiation at which it occurs.

X-linked or Bruton's-type agammaglobulinaemia, for example, is an immunodeficiency disease known to result from a defect in B-cell differentiation. Although the differentiation of T lymphocytes proceeds near normally, in general, few mature B lymphocytes develop. As a result, the levels of all major classes of immunoglobulins are drastically reduced in this disease, and this defect makes most patients vulnerable to bacterial infections. X-linked agammaglobulinaemia may be treated by periodic intramuscular inoculations of immune globulin, that provide a minimal level of antibody protection against at least some infectious diseases. Repeated intramuscular injections, however, are costly, painful, often lead to local scarring, and may produce severe anaphylactic-like reactions. Repeated intravenous plasma infusion is an alternative therapy which is occasionally used. Each infusion, however, takes several hours, and requires plasma from a single donor, who must be free of microbial contamination, e.g., hepatitis virus-free. Immune globulin formulated for intravenous administration is also available, but extremely costly.

In Wiskott-Aldrich syndrome, immunological defects occur in both T and B lymphocytes. The number of T cells in Wiskott-Aldrich syndrome patients decreases progressively, while the number of B cells expands, IgM levels are lower, and total IgG concentrations are normal. Afflicted patients do not make antibodies to polysaccharide antigens, and respond poorly to protein antigens. This disease may only be treated at the present time by bone marrow transplantation, but only if a histocompatible donor is available.

It is, therefore, highly desirable to identify relatively inexpensive, non-toxic, easily administered agents which are suitable for enhancing the immune response of mammals afflicted with an immunodeficiency disease(s), and/or for accelerating and enhancing the immune response of normal and elderly mammals when clinically indicated. It is also desirable in some instances to inhibit or suppress an immune response, such as in transplants.

SUMMARY OF THE INVENTION

The present invention relates to a composition suitable for modulating a mammal's immune response, e.g., B and/or T lymphocyte activity(ies). The composition of the invention is useful for treating mammals afflicted with an immune deficiency disease(s), including but not limited to, those of genetic and viral origin, as well as for enhancing normal antibody responses, e.g., vaccine therapy. In addition, the composition is also useful for inducing immunosuppression in mammals, such as is often necessary in transplant recipients, and in those afflicted with autoimmune disease.

The composition of the invention comprises an amount of a therapeutic agent selected from the group consisting of inositol stereoisomers, derivatives thereof, salts thereof, and mixtures thereof. The composition is provided in various forms and formulations, and as an implant, a topical and transdermal formulation, as a slow release formulation, as an inhalable and vaporizable composition, and in injectable form. The composition may be part of a kit, along with instructions for the administration of the therapeutic agent, and optionally syringe(s) and needles, an inhalant device, a transdermal device, and the like.

BRIEF DESCRIPTION OF THE DRAWINGS

FIG. 1(c) shows a primary antibody response (IgG) to SRBC by immunodeficient XID mice fed the control diet (left column, ●) or the same diet supplemented with 0.4% (w/w) myo-inositol (middle column, ○) and immunocompetent mice fed the control diet (right column, X).

DETAILED DESCRIPTION OF THE PREFERRED EMBODIMENTS

Figure 1A:
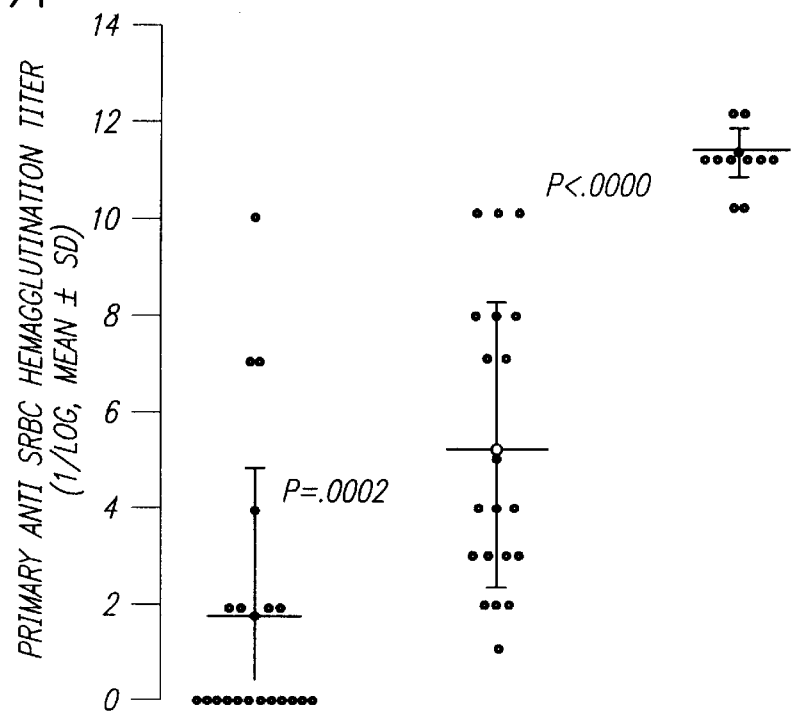
FIG. 1(a) shows a primary antibody response (total) to Sheep Red Blood Cells (SRBC) by immunodeficient XID mice fed the control diet (left column, ●) or the same diet supplemented with 0.4% (w/w) myo-inositol (middle column, ○) and immunocompetent mice fed the control diet (right column, X)

This invention arose from a desire by the inventors to improve on prior technology for modulating the immune response of normal subjects or of those which, as a result of defects in their B and/or T lymphoid cells, develop an immunodeficiency disease and, more generally, exhibit a partial impairment of immune function. The method of the invention modulates (increases/decreases) the immune response of a mammal by administering a therapeutic agent selected from inositol stereoisomers, derivatives thereof, salts thereof, and mixtures thereof, in an amount effective to alter (increase/decrease) the mammal's B and/or T lymphocyte activity(ies).

More specifically, as used herein, the term "modulating" and its various grammatical variations, refer to either the enhancement, inhibition, or suppression of immune response in a mammal. As used herein, the term "inositol" refers to non-phosphorylated inositol forms, a six carbon sugar alcohol, and encompasses all stereoisomers of inositol, such as myo-inositol, scyllo-inositol, epi-inositol, cis-inositol, allo-inositol, neo-inositol, chiro-inositol, muco-inositol, dextro-inositol, levo-inositol, their derivatives, their salts, and mixtures of any two or more thereof. Preferred inositol stereoisomers for use in the practice of the present invention include myo-inositol, scyllo-inositol, chiro-inositol, their derivatives, their salts, and mixtures of any two or more thereof. Inositol "salts" contemplated for use in the practice of the present invention include any and all pharmaceutically acceptable salts. Examples are salts of therapeutically acceptable organic acids, such as acetic, fumaric, lactic, maleic, citric, malic, succinic, toluene-sulfonic acid, and the like, salts of polymeric acids, such as tannic acid, alginic acid, carboxymethylcellulose, and the like, and salts of inorganic acids, such as hydrochloric acid, sulfuric acid, and the like. Others, however, may also be utilized. Inositol "derivatives" employed in the practice of the present invention include those which have been modified to vary the hydrophilic or lipophilic character of the stereoisomeric inositol molecules. Such modifications may be desirable to tailor the solubility characteristics of the inositols to a particular mode or route of administration. For example, lipophilic side chains, including $C_1$–$C_{20}$ hydrocarbon chains, which may be saturated or unsaturated and contain one or more non-hydrophilic substituents, may be added, as well as conjugating the inositols to a lipophilic molecule to enhance its lipid solubility. Alternatively, the addition of hydrophilic side chains or inositols conjugates to a hydrophilic molecule will enhance the hydrophilicity of the inositols, including $C_1$–$C_{20}$ hydrocarbon chains which may be unsaturated, and may have hydrophilic substituents such as HO, HS, $NH_2$, halo, keto, and the like. Exemplary inositol derivatives contemplated for use in the practice of the present invention include amine-substituted, halogen-substituted, deoxy-, keto-, and sulfo-inositol analogues, and the like, as well as combinations of any two or more substituents thereof. Preferred inositol derivatives include substituted inositol derivatives, including hydroxy, amino, halo, e.g., fluoro, deoxy, keto, and sulfo inositol analogues, among other hydrophilic substituents, and combinations thereof, as well as the corresponding salts. As used herein, the term "immune response" refers to the response by B and/or T lymphocytes to an antigenic agent, the term "antigenic agent," refers to both foreign and self antigens, and the terms "B lymphocyte response" and "B lymphocyte activity" are used interchangeably to refer to the proliferation and maturation of B lymphocytes with synthesis and secretion of antibodies or inhibition of antibody synthesis. The terms "antibody" and "immunoglobulin" are used interchangeably herein to refer to a protein produced by B lymphocytes in response to foreign or self antigenic substances and includes any one or more immunoglobulins of the IgM, IgG, IgA, IgE, and/or IgD classes. The terms "T lymphocyte response" and "T lymphocyte activity" are used here interchangeably to refer to the proliferation and/or differentiation of T lymphocytes into helper T lymphocytes or cytotoxic killer or suppressor T lymphocytes.

An immune response may be detected in a mammal by various methods that are well known to those of ordinary skill in the art. Variations in immune response, for example, may be detected by monitoring the level of antibody in serum, B and/or T lymphocyte proliferation, or T cell differentiation into helper and/or effector or suppressor T cells, as described below in Examples 1 to 8 and 16.

The therapeutic agent of this invention, with the exception of scyllo-inositol, is typically administered to a subject to alter B and/or T lymphocyte activity(ies) at a dose of about 20 to about 8,000 mg/kg/day, and preferably at about 30 to about 5,000 mg/kg/day. Other amounts, however, may also be administered. Scyllo-inositol was found by the inventors to be about ten-fold more potent in modulating immune response than most of the other inositol stereoisomers. Scyllo-inositol, thus, is typically administered to a mammal to alter its B and/or T lymphocyte activity at a dose of about 2 to about 800 mg/kg/day, and preferably about 3 to 500 mg/kg/day. Higher or lower doses of these agents, however, may also be administered.

The present inventors have discovered that the agent of the invention modulates a subject's immune response in a dose dependent manner. When the agent is administered at relatively low doses, it effectively enhances a mammal's immune response and, surprisingly, when administered at relatively high doses, inositol effectively inhibits or suppresses the mammal's immune response. The present invention, thus, provides a method for enhancing a mammal's immune response by administering to the mammal an immune response-enhancing amount of inositol effective for enhancing the mammal's B and/or T lymphocyte activity (ies). As used herein, the term "immune response-enhancing amount of the agent" refers to a dose of the agent that, when administered to a mammal, effectively enhances its B and/or T lymphocyte activity(ies), when compared to a control mammal. The term "control mammal" refers here to the mammal prior to the administration of the agent of this invention or, alternatively, to a subject (mammal) that is immunologically similar to, and of the same species as, the treated mammal, but that has not been administered the agent. As used herein, the term "immunologically identical" refers to immune systems that respond in a similar or the same manner to the same antigenic agents.

The dose range for enhancing immune response may vary somewhat depending on the form of the agent employed, such as, the particular stereoisomer, derivative, or salt employed. One of ordinary skill in the art, however, may readily determine the range of immune response-enhancing doses of the therapeutic agent by means known in the art, e.g., by generating a dose-response curve (i.e., immune response vs. dose) for any particular form of therapeutic agent. The enhancement of immune response may be detected, for instance, as either an acceleration of, or a net increase in, antibody production, as an increase in B and/or T lymphocyte proliferation, or as an increase in T cell differentiation into helper and/or effector or suppressor T cells. The dose of the therapeutic agent administered to modulate immune response will, of course, also vary with factors such as the pharmacodynamic characteristics of the agent employed, its mode and route of administration, the age, health, and weight of the recipient, the nature and extent of the symptoms, the kind of concurrent treatment(s), the frequency of treatment, the effect desired, and the like. With the exception of scyllo-inositol, the therapeutic agent of the invention is typically administered in an amount of about 20 to about 1,600 mg/kg/day to enhance a mammal's immune response, preferably about 200 to about 1,200 mg/kg/day, and most preferably about 400 to about 800 mg/kg/day. Scyllo-inositol is typically administered in an amount of about 2 to about 160 mg/kg/day to enhance immune response in a mammal, preferably about 20 to about 120 mg/kg/day, and most preferably about 40 mg/kg/day to about 80 mg/kg/day. Other amounts may be utilized, however, for specific agent forms, as determined by an artisan. When the therapeutic agent of the invention is administered in doses within the above indicated ranges, the mammal's immune response is typically enhanced by at least about 50%, may even result in at least about 100% enhancement, and in some instances in at least about 300% or greater enhancement of immune response, when compared to a control.

In another embodiment, the present method inhibits or suppresses immune response in a mammal by administration of an immunosuppressing amount of the therapeutic agent effective for inhibiting or suppressing the mammal's B and/or T lymphocyte activity(ies). As used herein, the term "immunosuppressing amount of the agent" refers to a dose of the therapeutic agent effective for suppressing B and/or T lymphocyte activity(ies) or for enhancing suppressor T cell activity, when compared to control. The exact dose range for suppressing immune response may vary somewhat depending on the form of therapeutic agent employed. One of ordinary skill in the art, however, will be able to readily determine the range of immunosuppressing dose as described above for any particular form of the agent. The inhibition or suppression of immune response may be detected as either a deceleration of, or as a net decrease in, antibody production, as a decrease in B and/or T lymphocyte proliferation, as a decrease in T cell differentiation into helper or effector T cells, or as an increase in suppressor T cells. The therapeutic agent, except for scyllo-inositol, is typically administered at a dose of about 2,000 to about 8,000 mg/kg/day to inhibit or suppress a mammal's immune response, preferably about 2,500 to about 6,000 mg/kg/day, and most preferably about 3,000 to about 4,000 mg/kg/day. Scyllo-inositol, on the other hand, is typically administered at a dose of about 200 to about 800 mg/kg/day to inhibit, reduce, or suppress immune response, preferably about 250 to about 600 mg/kg/day, and most preferably about 300 to about 400 mg/kg/day. The administration of the therapeutic agent as taught by the inventors will typically inhibit or suppress a mammal's immune response by at least about 30%, in some cases at least about 50%, and at times even more than 70%, as compared to a control.

The present inventors have, thus, discovered that the present therapy is particularly effective at modulating, either increasing or decreasing, B and/or T lymphocyte activity (ies) in normal and immunodeficient mammals, and in mammals afflicted with auto-immune disease. As used herein, the term "normal mammal" refers to mammals having B and/or T lymphocyte function(s) within the normal range in the population. For example, an immune response-enhancing amount of the agent may be administered to a normal mammal to enhance his/her/its normal antibody response to vaccine therapy. Alternatively, an immunosuppressing amount of the agent may be administered to a normal mammal which is a transplant recipient, to inhibit transplant rejection. As contemplated in the practice of the present invention, an immune response-enhancing dose of the therapeutic agent may be administered to an immunodeficient mammal to enhance its B and/or T lymphocyte activity(ies). Likewise, an immunosuppressing dose of the agent may be administered to a subject afflicted with an auto-immune disease(s), and to transplant subjects to suppress B and/or T lymphocyte activity(ies), and to, thereby, avoid the known detrimental, and sometimes fatal, effects which may afflict the subject. The term "immunodeficient mammal" refers to a mammal afflicted with an immunodeficiency disease based on impaired or reduced B and/or T lymphocyte function(s). Examples of these are immunodeficiency diseases associated with aging and those of genetic origin, including, X-linked (Bruton-type) agammaglobulinaemia, hyperimmunoglobulin M syndrome, CD40 ligand deficiency, IL-2 receptor deficiency, γ chain deficiency, common variable immunodeficiency, Chediak-Higashi syndrome, Wiskott-Aldrich syndrome, and the like, and immunodeficiency diseases of viral origin, including HIV infection of T lymphocytes, and the like. As used herein, the term "auto-immune disease" refers to diseases such as systemic lupus erythematosus, rheumatoid arthritis, auto-imnmune thyroiditis, scleroderma, inflammatory bowel disease, and the like.

The present invention contemplates the administration of the therapeutic agent in any pharmaceutically acceptable formulation. The agent may be administered in the form of a solid, such as tablets, dragees, capsules, powders, suppositories, etc., and as a solution, suspension, or emulsion in a carrier. Particularly desirable are formulations for systemic and topical administration, e.g., oral, injectable, topical, transdermal, including those for iontophoretical delivery, implantable, and vaginal, anal, intranasal, intrapulmonary, and other types of formulations, which may be prepared by methods known in the art. Solid and liquid carriers are suitable, and are known in the art. Liquid carriers typically used in preparing solutions, suspensions, and emulsions, which are contemplated for use in the practice of the present invention include water, salt solutions, such as saline, pharmaceutically acceptable organic solvent(s) and their mixtures, pharmaceutically acceptable oils or fats, and mixtures of any and all of the above. The carrier may contain other therapeutic agents and suitable pharmaceutically acceptable additives such as solubilizers, emulsifiers, nutrients, buffers, preservatives, suspending agents, thickening agents, viscosity regulators, and stabilizers, among others. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier may also be an oily ester such as ethyl oleate, isopropyl myristate, and the like. Other pharmaceutically acceptable forms include microparticles, microcapsules, liposomal encapsulates, and the like, as well as their combinations of the agent of the invention, alone or with one or more other therapeutic agents may be formulated into sustained release microparticles or microcapsules. Materials suitable for the microparticle matrix include materials such as starch, polyvinyl alcohol, polyvinylpyrrolidinone, polyacrylic acid, and the like, as well as combinations of any two or more thereof. Biodegradable polymers suitable for use as a microparticle or microcapsule matrix include, for example, poly-l-lactide, poly-dl-lactide, polyglycolide, poly(glycolide-co-dl-lactide), polyanhydrides, polyorthoesters, poly(alpha-hydroxybutyric acid), poly-p-dioxinone, and block polymers of polyglycolide, trimethylene carbonate, polyethylene oxide, proteins, polysaccharides, and derivatives and mixtures thereof. The microparticles and microcapsules containing the agent may be prepared employing methods which are well known in the art, e.g., by solvent evaporation, phase separation, and interphase reaction methods, spray drying, physical methods, and the like. As already indicated, the present agent may also be encapsulated into liposomes, and the microparticles, microcapsules, and/or liposomes loaded with the agent may then be suspended or emulsified in a suitable liquid carrier.

The present agent may be administered in a variety of ways, including topical, enteral, and parenteral routes of administration. For example, suitable modes of administration include subcutaneous, transdermal, transmucosal, including iontophoretic, intravenous, subcutaneous, transnasal, intrapulmonary, transdermal, oral, rectal, vaginal, implantable and the like, as well as their combinations. The particular pharmaceutically acceptable form of the therapeutic agent employed will depend on the route of administration selected. The agent may be, for example, administered in a form that enhances its bioavailability when compared with standard oral formulations. Suitable forms include a lipid carrier system that promotes the oral absorption of compounds through the intestinal epithelium. Examples of these systems are oil-in-water, and water-in-oil emulsions. Exemplary oils that are contemplated for use in oil-in-water and water-in-oil based systems include castor oil, olive oil, soybean oil, safflower oil, coconut oil, cottonseed oil, their combinations, and the like. Other suitable forms that enhance the bioavailability of the orally administered agent of this invention include single surfactant, and mixed micelle systems. The agent may, for example, be orally administered in the form of a mixed micelle system containing linoleic acid and polyoxyethylene-hardened castor oil. Suitable surfactants contemplated for use in single and mixed micelle systems include polyoxyethylene ether, polyoxypropylene ether, polyoxyethylene lauryl, cetyl and cholesteryl ethers, polyoxyethylene derivatives of lanolin alcohols, and the like, as well as their mixtures.

When intravenous or subcutaneous administration is contemplated, the use of a solution of the therapeutic agent is preferred. For transdermal administration by iontophoresis, the agent is preferably administered in charged form, such as in the form of a salt. The salt may be in solution or in a gel reservoir. Therapeutic agent-containing gels may be used as a drug reservoir for many routes of administration. An agent containing gel may be prepared by blending inositol with a hydrogel-forming polymer such as polyvinyl alcohol, polyacrylamides, copolymers of propylene oxide and ethylene oxide, e.g., Pluronic®, polyvinylpyrrolidinone, gelatin, polymers and copolymers of maleic anhydride, polyacrylic acid and salts and derivatives thereof, polysaccharides, and salts and derivatives thereof, cellulosic polymers, and salts and derivatives thereof, polycarboxylic acids, and the like, as well as their mixtures. The agent may also be administered transdermally through the use of a skin patch, with a carrier. Suitable carriers are typically inert to the agent, non-toxic to the skin, and allow the delivery of the agent for systemic absorption into the blood stream via the skin. Carriers for transdermal absorption may include pastes, such as absorptive powders dispersed in petroleum or hydrophilic petroleum with the agent, with or without a carrier, or a matrix containing inositol. Preparations of agent-based compounds may also be administered topically as a solution, cream, lotion, or gel, formulated with pharmaceutically acceptable vehicles containing the agent. The agent may also be administered intra or transnasally or intrapulmonarily as an aerosol spray of a solution, suspension or emulsion, or as microparticles, microcapsules, or liposomes containing the agent. Also contemplated are formulations of the agent of this invention with pharmaceutically acceptable excipients. Suitable excipients contemplated for use as processing aids and drug delivery modifiers and enhancers include calcium phosphate, magnesium stearate, talc, monosaccharides, disaccharides, starch, gelatin, cellulose, methyl cellulose, sodium carboxymethyl cellulose, dextrose, polyvinylpyrrolidinone, low melting waxes, ion exchange resins, and the like, as well as their combinations. Typically, such formulations are prepared as tablets or capsules. Other formulations are, however, also within those contemplated in this patent.

The agent may be administered as a single dose or in multiple doses. Multiple doses may be administered either continuously, in intervals, or a combination of both. The agent, for example, may be administered as a single dose, optionally coupled with a follow-up dose. The follow-up dose may be administered by the same or different route of administration as a single or sustained dose. Accordingly, the present composition is presented in unit dosage form or in multiple dosage form, as well as in the form of a kit, which may be for self administration, along with instructions for the use of the therapeutic agent, and optionally a syringe(s) and needle(s), an inhaler or vaporizer, a transdermal patch, optionally for iontophoresis, and the like. The composition is also provided as a cream or gel for topical application, and as an implant. The manufacture of implants is known in the art and commercially available.

The invention will now be described in greater detail by reference to the following nonlimiting examples.

EXAMPLES

Example 1
Experimental Animals Utilized

Adult naive male and female B10.A(15R) and B10.A (18R) mice were used in Examples 9 through 15. Immunodeficient male XID mice and immunocompetent CBA/CaJ control mice were used in Examples 16 through 18.

Example 2
Cell Culture Conditions

All cultures were done in duplicate or triplicate, and replicate samples were generally within 5% of the mean. The culture medium was RPMI 1640 supplemented with L-glutamine, 10% heat inactivated fetal calf serum and penicillin and streptomycin (100 U and 100 $\mu$g/ml, respectively).

Example 3
Red Blood Cell (RBC) Primary Response Assay (Foci and PFC)

Primary responses to sheep red blood cells (SRBC) were elicited according to the following protocol in accordance with Tyan, P. S. E. M. B. 150:313–317 (1975), the relevant portions of which are incorporated herein by reference. Briefly, an underlay of washed SRBC (2%) in 1.5 ml of agar (0.25%) was placed in 35×10 mm tissue culture dishes (Falcon Plastics, Oxnard, Calif.) and 3 ml of spleen cell suspension were added after the agar had hardened. Myo-inositol (tissue culture grade, Sigma Chemical Co., St. Louis, Mo.) was added to the cultures at the indicated concentrations, and the cells were cultured at 37° C. in 5% $CO_2$ in air for 1 to 3 days. The medium and cells were then carefully removed and 1 ml of guinea pig complement (diluted 1:7) (Sigma Chemical Co., St. Louis, Mo.) was added to each dish. After 1½ hours at 37° C. and 2 hours at room temperature, the areas of focal hemolysis were counted.

Each area of hemolysis present in the agar was found to represent a cluster of specific antibody-forming cells (foci). When the cells were carefully removed from the agar and plated on another SRBC-agar underlay to detect single PFC (antibody forming cells), from 1 to 70 PFC were found for each area of hemolysis noted on the original plate. The results indicate that each area of hemolysis is the result of the production of specific antibody for the following reasons.

(I) It is complement dependent;
(II) Cells cultured on agar without SRBC did not contain SRBC-PFC on transfer, and
(III) Cells cultured on SRBC-agar did not contain PFC to horse RBC and vice-versa.

Example 4
Direct and Indirect PFC Assay (B Lymphocyte Proliferation Assay)

Cells from the spleens of mice immunized with SRBC in vivo (0.2 ml 20% SRBC administered intravenously) and cells taken from culture dishes at the termination of the experiments were assayed for direct (IgM) and indirect (IgG) PFC by methods described previously. Briefly, the cells were added to agar (0.5%) containing 2% SRBC, then incubated at 37° C. for 1½ hours; complement was added (1:7) and the plates were incubated for 1 hour. The number of direct (IgM) PFC were then counted. After counting the number of direct (IgM) PFC, goat anti-mouse IgG serum (1:100) (Sigma Chemical Co., St. Louis, Mo.) was added. The plates were incubated for 1 hour at 37° C., then for 2 hours at room temperature. The individual hemolytic areas were counted and the number of indirect (IgG) PFC calculated according to the following: Indirect (IgG) PFC=Total PFC minus Direct (IgM) PFC.

Example 5

Statistical Analysis

Means were compared using the paired t-test and the Mann-Whitney two sample test (NCSS statistical program; NCSS, Kayville, Utah). The most conservative p-value is reported without correction for multiple determinations.

Example 6

T Cell Proliferation Assay

T cell proliferation can be assayed according to the method described in Berkower, et al., J. Immunol. 135:2628–2634 (1985), incorporated herein by reference. T cells, such as those from peripheral blood, are incubated with or without inositol in a standard MLR (mixed lymphocyte reaction) or with antigen, such as SRBC, in 10% FCS/RPMI with antibiotics at 37° C. in a humidified, $CO_2$/air atmosphere×4–5 days. They are then labeled with 1 uCi $^3$H-thymidine (6.4 Ci/mM) for 18 hours under the same conditions, harvested and counted in a scintillation counter. For MLR, a stimulation index of 10.0 and/or a relative response of 30% above the negative/autologous control is considered significant. Stimulation indices between 2.0 and 10.0 or relative responses between 15% and 30% are considered equivocal.

Example 7

Helper T Cell Assay

Helper T cell activity can be assayed for in accordance with the method described by Marrack et al., J. Immunol. 140:2508–2514 (1988), incorporated herein by reference. B cells are primed with SRBC and then coincubated with primed T cells×4 days. The cells are then harvested and assayed for anti-SRBC PFC as described in B cell assays (see Examples 3 and 4).

Alternatively, $10^6$ cells/well from an IL-2 producing T cell line or splenocytes are cocultured with various concentrations of SRBC with/without inositol in 250 μl of 10% FCS/RPMI with antibiotics×24 hr at 37° C. in a humidified, $CO_2$/air atmosphere. (See, Weiss et al., J. Immunol. 133:123–127 (1984) and Urban et al., Cell 54:577–592 (1988), both incorporated herein by reference). Supernatant is obtained at the end of the incubation period, diluted, and added in IL-2 assay medium [DMEM supplemented with penicillin/streptomycin, L-glutamine (2 mM), 10% FCS, 10 mM Hepes, $5\times10^{-5}$M 2-mercaptoethanol] to new wells to bring the volume to a total of 100 μl/well. An equal volume (100 μl) of IL-2 dependent CTLL-20 or HT-2 cells ($5\times10^3$–$3\times10^4$/ml) is added to the supernatant containing wells and the testing is performed in triplicate. The cells are incubated 20–24 hours as previously, at which time 1 μCi $^3$H-thymidine (6.4 Ci/mM) is added to each well. Incubation is continued for 4–6 hours and the cells are harvested and counted in a scintillation counter. Control wells contain either no source of IL-2 or serial dilutions of a known amount of IL-2. Activity is expressed as U/ml when compared with controls. The limit of detection is 0.2 U/ml and the standard deviation is less than 10% of the mean.

Example 8

CTL (Killer Cell) Assay

Killer T cells may be assayed for in accordance with the methods described in Duke et al., J. Immunol. 141:2191–2194 (1988), Devos et al., Eur. J. Immunol. 14:1057–1060 (1984), Schmid et al, J. Immunol. 140:3610–3616 (1988), Jacobson et al., J. Immunol. 133:754–757 (1984), and Goistein, Nature 252:81–83 (1974), all incorporated herein by reference.

Cells from 6 wells each are harvested and pooled after 5 days incubation in the T cell proliferation assay. The cells are incubated with $^{51}$Cr labeled P815 target cells (10:1) and the percent specific release of chromium is calculated by sampling the supernatant and counting in a scintillation counter. The percent specific release is given by the following formula.

$$\% \text{ specific release} = \frac{cpm\,^{51}Cr\text{- spontaneous release} \times 100}{\text{total }^{51}Cr\text{ release - spontaneous release}}$$

Spontaneous release=cpm in wells without effector cells ($^{51}$CR labeled P815 only)

Total release=cpm in wells with $^{51}$Cr labeled P815 cells treated with 1% Triton-X Unsensitized targets (spontaneous release wells) show less than 1% specific lysis. Spontaneous release is usually 10–15%. Tests are significant which are 3 standard deviations above the mean (usually about 5% or more specific release).

Example 9

Effect of Inositol on Anti-SRBC Foci Formation & Antibody Forming Cells (PFC) in Spleen Cells from Naive Donors Spleen cells from B10A.(15R) and B10.A(18R) naive mice were cultured with sheep red blood cells (SRBC) in the presence or absence of myo-inositol (1.0, 4.0, and 8.0 mg/ml) as described in Examples 2 and 3. The results are shown in Table 1 below.

TABLE 1

Effect of Myo-inositol on Anti-SRBC Colonies of Antibody-forming Cells (Foci) and Antibody Forming Cells (PFC) per Focus in 3-Day Cultures of Spleen Cells from Naive Donors

| Assay | myo-inositol (mean ± s.d.)/(mg/ml) | | |
|---|---|---|---|
| | 1.0 | 4.0 | 8.0 |
| Foci[a] | 1.32 ± 0.56 | 1.10 ± 0.31 | 0.99 ± 0.84 |
| (n) | (8) | (19) | (6) |
| PFC/focus[b] | 1.56 ± 1.22 | 3.24 ± 2.90[c] | 1.65 ± 1.80 |
| (n) | (6) | (10) | (5) |

[a]The data were normalized as follows:

$$\frac{\text{Foci in cultures with added inositol}}{\text{Foci in cultures without inositol}}$$

[b]The data were normalized as follows:

$$\frac{\text{PFC per focus in cultures with added inositol}}{\text{PFC per focus in cultures without inositol}}$$

[c]p <0.01, paired t-test.

At a concentration of 4.0 mg/ml there were 3 times as many PFC/focus as in the control cultures. These results indicate that inositol is effective at significantly increasing the number of antibody-forming cells per focus during the culture period.

Example 10

Inositol Effect on In Vitro Primary Response to SRBC

Spleen cells from naive mice were cultured with SRBC in the presence or absence of 4.0 mg/ml myo-inositol as described in Examples 2 and 3. The number of foci generated was determined on days 1, 2, and 3. The results are shown in Table 2 below.

TABLE 2

Effect of Myo-inositol on In Vitro Primary Response to SRBC on Days 1, 2, and 3

| Inositol | Foci per Culture (Mean ± s.d.) (n) | | |
|---|---|---|---|
| (4 mg/ml) (n) | Day 1 (6) | Day 2 (6) | Day 3 (6) |
| No | 1.88 ± 1.06[a] | 25.8 ± 15.3 | 24.0 ± 9.4 |
| Yes | 5.33 ± 2.56[a] | 22.6 ± 16.6 | 23.1 ± 14.1 |

[a]$p = 0.004$, paired t-test.

The cultures with added inositol exhibited significantly more anti-SRBC producing cell foci than the controls on day 1. These results show that inositol accelerates B lymphocyte activity in normal mammals.

Example 11

Added Dietary Myo-inositol Effect on Spleen PFC 3 & 5 Days after Primary Challenge with SRBC Naive mice on a standard diet (Purina Laboratory Chow 5001) or an inositol-supplemented (0.4% w/w) diet were given 0.2 nml 20% SRBC intravenously. Three and five days later their spleens were assayed for PFC as described in Example 4. The results are shown in Table 3 below.

TABLE 3

Added Dietary Myo-inositol Effect on Spleen PFC 3 & 5 Days after Primary Challenge with SRBC[a]

| Inositol | Direct (IgM) PFC per Spleen (×10³) (Mean ± s.d.) | |
|---|---|---|
| (0.4%) (n) | Day 3 (7) | Day 5 (6) |
| No | 0.93 ± 0.45[b] | 39.9 ± 19.8 |
| Yes | 2.26 ± 1.08[b] | 37.2 ± 24.9 |

[a]Mice were started on the supplemented diet 2 days before challenge.
[b]$p < 0.01$, paired t-test.

The results indicate that naive mice on the inositol supplemented diet had twice the number of direct (IgM) PFC per spleen as the controls on day 3.

Example 12

Myo-inositol Effects In Vivo and/or In Vitro on Primary Immune Response to SRBC Naive mice were maintained on the control diet or placed on an inositol supplemented (0.4%) diet 4 days before their spleen cells were cultured with SRBC with or without added myo-inositol. Results are shown in Table 4 below.

TABLE 4

In Vivo and/or In Vitro Effects of Myo-inositol on Primary Immune Response to SRBC

| | Control Diet | | Myo-inositol Diet | |
|---|---|---|---|---|
| Myo-inositol in Culture (0.4%) | Direct Foci per Spleen[a] | Direct PFC per Focus[b] | Direct Foci per Spleen | Direct PFC per Focus |
| No | 26.2 | 0.97[c,e] | 28.4 | 2.01[d,e] |
| Yes | 28.5 | 2.52[c,f] | 29.4 | 0.49[d,f] |
| Std. Error of diff. | 1.94 | 1.00 | 8.32 | 0.47 |
| n | 19 | 10 | 5 | 5 |

[a]Mean (×10³) (Groups were compared using the paired t and Mann-Whitney tests)
[b]Cells recovered from cultures on day 3.
[c]$p = 0.028$
[d]$p = 0.024$
[e]$p = 0.037$
[f]$p = 0.034$ The number of foci per culture was not affected by exposure of the spleen cells to myo-inositol in vivo and/or in vitro; however, direct PFC/focus were increased when the spleen cells were exposed to inositol either in vivo or in vitro and they were markedly decreased when exposed both in vivo and in vitro. These results indicate that at higher doses, inositol suppresses B lymphocyte activity.

Example 13

Myo-inositol Effect on Indirect (IgG)/Direct (IgM) PFC Ratio upon SRBC Primary Challenge (with/without Secondary Stimulation)

Naive mice were fed the control diet or an inositol-supplemented (0.4%) diet and given 0.2 ml 20% SRBC intravenously. Five days later their spleens were assayed for PFC and their spleen cells were cultured with SRBC with or without added myo-inositol. Results are shown in Table 5 below.

TABLE 5

In Vivo and/or In Vitro Myo-inositol Effect on Indirect (IgG)/Direct (IgM) PFC Ratio[a]

| Myo-inositol (0.4% Culture) (n) | PFC 5 Days after Challenge (7) | PFC After 3 Days of Culture[b] (6) |
|---|---|---|
| No | 1.0 ± 0.51 | 1.12 ± 0.85[c] |
| Yes | N/A | 0.43 ± 0.03[c] |

[a]Ratio ± s.d. (n);

$$\frac{\text{Foci in cultures with added inositol}}{\text{Foci in cultures without inositol}}$$

[b]Secondary response.
[c]$p < 0.001$, paired t-test.

These results indicate that the ratio of indirect (IgG) to direct (IgM) PFC was unaffected by a single in vivo or in vitro treatment with inositol, but IgG PFC were severely decreased on double exposure when measured at the end of a secondary response.

Example 14

3-Day In Vitro Myo- and Scyllo-inositol Effect on Anti-SRBC Foci & PFC Generation in Spleen Cells from Naive Donors Spleen cells from naive mice were cultured for three days with sheep red blood cells (SRBC) in the presence of either myo-inositol (1.0, 4.0 or 8.0 mg/ml) or scyllo-inositol (0.2, 0.4, or 0.8 mg/ml). The results are shown in Table 7 below.

TABLE 7

3-Day In Vitro Myo- and Scyllo-inositol Effect on anti-SRBC Foci & PFC Generation in Spleen Cells from Naive Donors

| Assay | Myo-inositol (mg/ml) | | | Scyllo-inositol (mg/ml) | | |
|---|---|---|---|---|---|---|
| (mean ± S.D.) | 1.0 | 4.0 | 8.0 | 0.2 | 0.4 | 0.8 |
| Foci[a] | 1.32 ± 0.56 | 1.10 ± 0.25 | 0.99 ± 0.84 | 1.25 ± 0.45 | 1.45 ± 0.45 | 0.82 ± 0.29 |
| (n) | (8) | (19) | (6) | (7) | (8) | (7) |
| PFC/Focus[b] | 1.56 ± 1.22 | 2.98 ± 2.67[c] | 1.65 ± 1.80 | 1.45 ± 0.26[d] | 1.82 ± 0.70[e] | 1.60 ± 0.79 |
| (n) | (6) | (11) | (5) | (5) | (5) | (5) |

[a]Data were normalized: foci in cultures with inositol/foci in cultures without it.
[b]PFC per focus in cultures with agent/PFC per focus in cultures without it.
[c]p = 0.033
[d]p = 0.019
[e]p = 0.003

These results indicate that the number of antibody forming cells per focus increased nearly three times when cultured in 4.0 mg/ml myo-inositol. Likewise, the number of antibody forming cells per focus increased nearly two times when cultured in 0.4 mg/ml scyllo-inositol.

Example 15
1-Day In Vitro Myo- and Scyllo-inositol Effect on anti-SRBC Foci & PFC Generation in Spleen Cells From Naive Donors Spleen cells from naive mice were cultured for one day with SRBC in the presence of either myo-inositol (2.0, 4.0 or 8.0 mg/ml) or scyllo-inositol (0.2, 0.4 or 0.8 mg/ml). The results are shown in Table 8 below.

TABLE 8

1-Day In Vitro Myo- and Scyllo-inositol Effect on anti-SRBC Foci & PFC Generation in Spleen Cells From Naive Donors

| Assay | Myo-inositol(mg/ml) | | | Scyllo-inositol (mg/ml) | | |
|---|---|---|---|---|---|---|
| (mean ± S.D.) | 2.0 | 4.0 | 8.0 | 0.2 | 0.4 | 0.8 |
| Foci[a] | 1.46 ± 0.29 | 2.62 ± 0.94 | 1.60 ± 0.17 | 1.84 ± 0.69 | 2.90 ± 0.90 | 2.63 ± 1.2 |
| (n) | (3) | (3) | (3) | (3) | (3) | (3) |
| PFC/Focus[b] | 1.03 ± 0.15 | 1.73 ± 0.53 | 1.10 ± 0.14 | 1.52 ± 0.70 | 1.85 ± 0.07[c] | 2.19 ± 0.56[d] |
| (n) | (3) | (3) | (3) | (3) | (3) | (3) |

[a]Data were normalized: foci in cultures wiffi inositol/foci in cultures without it.
[b]PFC per focus in cultures with inositol/PFC per focus in cultures without it.
[c]P < .01
[d]P < .05

These results indicate that scyllo-inositol is about as effective as myo-inositol at enhancing the proliferation of antibody forming cells at one tenth the dosage.

Example 16
Inositol Effect on Primary anti-Sheep Red Blood Cell Response (IgM and IgG) in Immunodeficient XID Mice Mouse X-linked immunodeficiency results from a failure of B cells to become phenotypically and functionally mature. B cells from XID mice do not respond to thymus-independent antigens, have reduced IgM and IgG$_3$ serum immunoglobulins, and have abnormal responses to several activation signals, such as immunoglobulin crosslinking, interleukin-5 and interleukin-10. This suggests that B cells of XID mice do not respond to essential signals for B cell proliferation, activation, and maturation.

Forty male CBA/CaHN-XID mice were maintained on a Purina 5001 diet. Seven days before being bled, 20 of the mice were started and continued on Purina 5001 supplemented with 0.4% (w/w) tissue-culture grade myo-inositol (Sigma Chemical Co., St. Louis, Mo.). After two days, all of the XID mice and 10 immunocompetent CBA/CaJ control mice were given 0.2 ml 20% SRBC (BBL) intravenously. Five days later, the mice were bled from the retroorbital plexus. Hemagglutination titers were determined by standard methods as described in Scher, I., et al., Immunology 123:477-486 (1979), incorporated herein by reference, on serum (not treated with dithiothreitol) and after treatment with dithiothreitol (Sigma Chemical Co., St. Louis, Mo.). Assays were performed at least twice on all samples and IgM titer was computed as the titer of total antibody (not treated with dithiothreitol) minus the titer of dithiothreitol-treated serum (IgG). Means were compared using the Mann-Whitney two sample test (NCSS statistical program, NCSS, Kayville, Utah). The most conservative p-value is reported without correction for multiple determinations. The results are shown in FIG. 1.

The results indicate that although XID mice given the inositol supplemented diet produced less anti-SRBC hemagglutination antibody than immunocompetent controls fed the standard diet, they produced significantly more anti-SRBC hemagglutinating antibody than did XID mice on the control diet. The increased antibody noted in the experimental group was largely, if not entirely, IgM.

Example 17
Inositol Effect on anti-SRBC Cell Production in Response to Primary SRBC Challenge At the time the mice from Example 16 were bled to assay the primary antibody response to SRBC, some were sacrificed to determine the number of anti-SRBC antibody producing cells (PFC) in their spleens.

Figure 2:
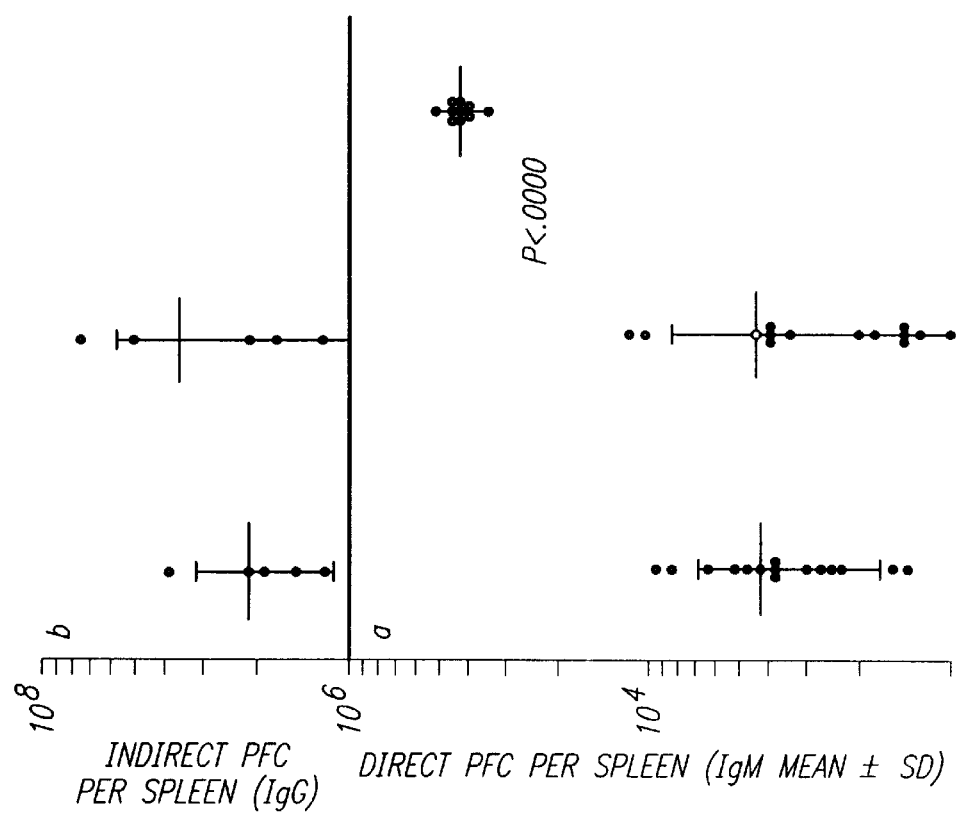
FIG. 2 shows the anti-SRBC antibody-forming cells (PFC) response as measured by the production of (a) IgM and (b) IgG in the spleens of immunodeficient XID mice fed the control diet (left column, ●) or the same diet supplemented with 0.4% (w/w) myo-inositol (middle column, ○) and immunocompetent mice fed the control diet (right column, X) 5 days after the primary injection of SRBC.

Total splenic PFC were determined on XID mice from each diet group and on 10 control immunocompetent mice described in Example 16 using the method described in Tyan, M., Proc. Soc. Exp. Biol. Med., 150:313–317 (1975), incorporated herein by reference. Indirect PFC were developed with a goat anti-mouse IgG serum (Sigma Chemical Co., St. Louis, Mo.). Results are shown in FIG. 2. The groups were compared using the Mann-Whitney test.

The results indicate that the supplemented diet had no significant effect on the number of IgM or IgG PFC found in the spleens of XID mice five days after primary injection of SRBC. The XID mice had 10 times fewer splenic IgM PFC than did the immunocompetent controls.

Figure 3:
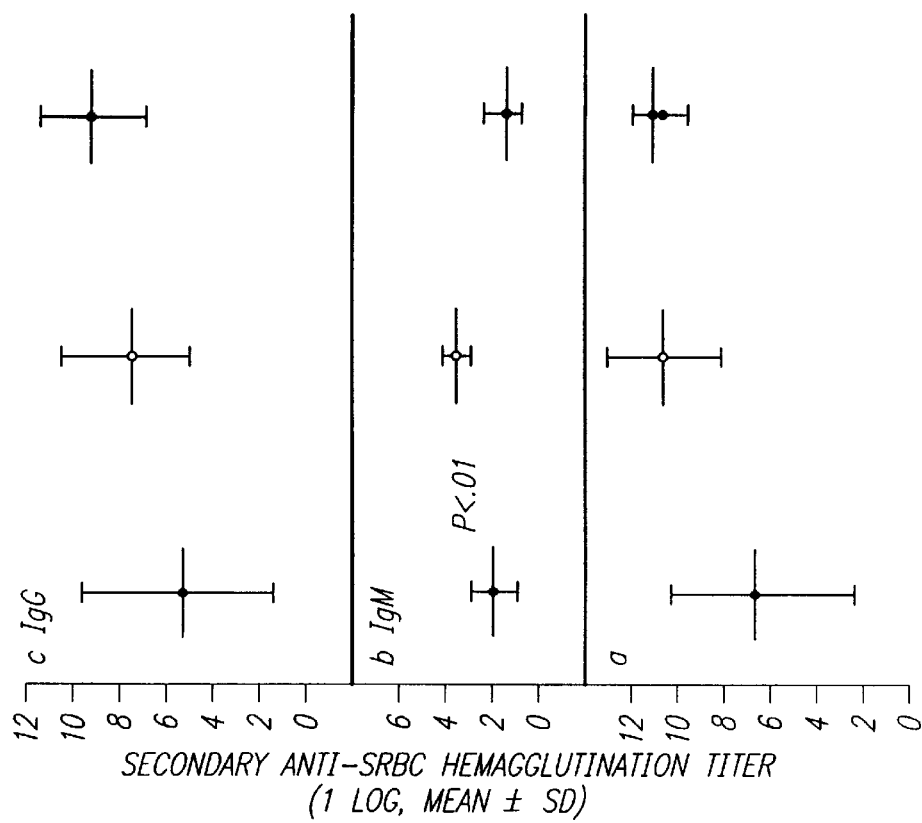
FIG. 3 shows the secondary antibody responses as measured by the production of (a) total antibody, (b) IgM, and (c) IgG to SRBC by XID mice fed the control diet (left column, ●) or the same diet supplemented with 0.4% (w/w) myo-inositol (middle column, ○) and immunocompetent mice fed the control diet (right column, X).

Example 18
Inositol Effect on Secondary anti-SRBC Response (IgM and IgG) in Immunodeficient XID Mice Five mice from each of the groups described in Example 16 were given a second intravenous injection of 0.2 ml 20% SRBC one week after being bled the first time. Five days later they were bled and hemagglutination titers were determined as described in Example 16 above. The results are shown in FIG. 3.

The results indicate that XID mice fed the diet supplemented with inositol had significantly higher titers of IgM antibody after rechallenge with SRBC than did XID mice or the immunocompetent controls given the standard diet. No significant differences in IgG titers were observed among the groups. Thus, these results, coupled with the results from Example 16 indicate that XID mice fed a diet supplemented with 0.4% (w/w) myo-inositol were found to have increased levels of IgM anti-SRBC hemagglutinating antibody after primary immunizations as compared to XID mice fed a control diet, and increased IgM anti-SRBC hemagglutination after secondary immunization as compared to both XID and immunocompetent mice fed control diets.

While the invention has been described in detail with reference to certain preferred embodiments, it will be understood that modifications and variations are within the spirit and scope of that which is described and claimed.

What is claimed as novel & unobvious in Letters Patent of the United States is:

1. A dose dependent method of enhancing, inhibiting or suppressing a mammal's immune response, comprising administering to a mammal in need of the treatment a dose dependent amount of a cell permeable therapeutic agent selected from the group consisting of inositol stereoisomers, inositol stereoisomer derivatives, inositol stereoisomer salts and mixtures of the inositol stereoisomers, inositol stereoisomer derivatives and inositol stereoisomer salts, effective to enhance, inhibit or suppress the mammal's B and/or T lymphocyte activity(ies); wherein to enhance the mammal's immune response the agent is administered in an amount of about 20 to about 1.600 mg/kg/day, and to inhibit or suppress the mammal's immune response the agent is administered in an amount of about 200 to about 8,000 mg/kg/day.

2. The method of claim 1, wherein
  the inositol stereoisomers are selected from the group consisting of myo-inositol, epi-inositol, cis-inositol, allo-inositol, neo-inositol, chiro-inositol, muco-inositol, dextro-inositol, levo-inositol, salts thereof and mixtures thereof with scyllo-inositol, derivatives thereof and salts thereof; and
  the inositol stereoisomer derivatives are selected from the group consisting of amino-inositol, fluoro-inositol, deoxy-inositol, keto inositol and sulfo-inositol, mixtures thereof, salts thereof and mixtures thereof with inositol stereoisomers, derivatives thereof and salts thereof.

3. The method of claim 1, wherein the therapeutic agent comprises scyllo-inositol, salts thereof and mixtures thereof with inositol stereoisomers, derivatives thereof or salts thereof; and
  the inositol stereoisomer derivatives are selected from the group consisting of amino-scyllo-inositol, fluoro-scyllo-inositol, deoxy-scyllo-inositol, keto-scyllo-inositol, and sulfo-scyllo-iniositol, mixtures thereof, salts thereof and mixtures thereof with scyllo-inositol stereoisomers, derivatives thereof and salts thereof.

4. The method of claim 1, wherein the mammal is selected from the group consisting of clinically normal and immunodeficient subjects, subjects afflicted by auto-immune conditions, and transplant subjects.

5. A method for enhancing a mammal's immune response, comprising administering to a mammal in need of the treatment a cell permeable therapeutic agent selected from the group consisting of inositol stereoisomers, inositol stereoisomer derivatives, inositol stereoisomer salts, and mixtures of the inositol stereoisomers, inositol stereoisomer derivatives and inositol stereoisomer salts, in an amount effective to enhance the mammal's T and/or B lymphocyte (s) activity(ies).

6. The method of claim 5, wherein the therapeutic agent is administered in an amount effective for producing an at least about 50% enhancement of the mammal's B and/or T lymphocyte activity(ies).

7. The method of claim 6, wherein the therapeutic agent is administered in an amount effective for an at least about 100% enhancement of the mammal's B and/or T lymphocyte activity(ies).

8. The method of claim 7, wherein the therapeutic agent is administered in an amount effective for producing at least an about 300% enhancement of the mammal's B and/or T lymph-ocyte activity(ies).

9. The method of claim 5, wherein the therapeutic agent is an inositol stereoisomer selected from the group consisting of myo-inositol, epi-inositol, cis-inositol, allo-inositol, neo-inositol, chiro-inositol, muco-inositol, dextro-inositol, levo-inositol, derivatives thereof, salts thereof and mixtures thereof with scyllo-inositol, derivatives thereof and salts thereof.

10. The method of claim 5, wherein the therapeutic agent is an inositol derivative selected from the group consisting of amino-inositol, fluoro-inositol, deoxy-inositol, keto-inositol, and sulfozinositol, mixtures thereof, salts thereof, and mixtures thereof with inositol stereoisomers, scyllo-inositol, derivatives thereof and salts thereof.

11. The method of claim 9, wherein the therapeutic agent is administered in an amount of about 20 to about 1,600 mg/kg/day.

12. The method of claim 9, wherein the therapeutic agent is administered in an amount of about 200 to about 1,200 mg/kg/day.

13. The method of claim 9, wherein the therapeutic agent is administered in an amount of about 400 to about 800 mg/kg/day.

14. The method of claim 5, wherein the therapeutic agent comprises scyllo-inositol, derivatives thereof, salts thereof or mixtures thereof with inositol stereoisomers, derivatives thereof or salts thereof.

15. The method of claim 14, wherein the scyllo-inositol is administered in an amount of about 2 to about 160 mg/kg/day.

16. The method of claim 15, wherein the scyllo-inositol is administered in an amount of about 20 to about 120 mg/kg/day.

17. The method of claim 16 wherein the scyllo-inositol is administered in an amount of about 40 to about 80 mg/kg/day.

18. The method of claim 5, wherein the mammal is immunodeficient.

19. The method of claim 5, wherein the mammal is clinically normal.

20. A method of boosting the immune response of a mammal to a vaccine, comprising
   (a) conducting the method of claim 5; and
   (b) administering a vaccine to the mammal.

21. The method of claim 20, wherein step (a) is conducted prior to, or simultaneously with, step (b).

22. The method of claim 20 wherein step (b) is repeated at a certain time interval.

23. The method of claim 20, wherein step (a) is repeated at a certain time interval.

24. A method for inhibiting or suppressing a mammal's immune response, comprising
   administering to a mammal in need of the treatment a cell permeable therapeutic agent selected from the group consisting of inositol stereoisomers, inositol stereoisomer derivatives, inositol stereoisomer salts, and mixtures of the inositol stereoisomers, inositol stereoisomer derivatives and inositol stereoisomer salts, in an amount effective to inhibit or suppress the mammal's B and/or T lymphocyte activity(ies).

25. The method of claim 24 wherein the therapeutic agent is administered in an amount effective for inhibiting or suppressing at least about 30% of the mammal's B and/or T lymphocyte activity(ies).

26. The method according to claim 25, wherein the therapeutic agent is administered in an amount effective for inhibiting or suppressing at least about 50% of the mammal's B and/or T lymphocyte activity(ies).

27. The method of claim 26, wherein the therapeutic agent is administered in an amount effective for inhibiting or suppressing at least about 70% of the mammal's B and/or T lymphocyte activity(ies).

28. The method of claim 24, wherein the therapeutic agent is an inositol stereoisomer selected from the group consisting of myo-inositol, epi-inositol, cis-inositol, allo-inositol, neo-inositol, chiro-inositol, muco-inositol, dextro-inositol, levo-inositol, derivatives thereof selected from the group consisting of amino-inositol, fluoro-inositol, deoxy-inositol, keto-inositol and sulfo-inositol, salts thereof and mixtures thereof with scyllo-inositol, scyllo-inositol derivatives selected from the group consisting of amino-scyllo-inositol fluoro-scyllo-inositol, deoxy-scyllo-inositol, keto-scyllo-inositol and sulfo-scyllo-inositol and salts thereof.

29. The method of claim 28, wherein the therapeutic agent is administered in an amount of about 2,000 to about 8,000 mg/kg/day.

30. The method of claim 29, wherein the therapeutic agent is administered in an amount of about 2,500 to about 6,000 mg/kg/day.

31. The method of claim 30, wherein the therapeutic agent is administered in an amount of about 3,000 to about 4,000 mg/kg/day.

32. The method of claim 24, wherein the therapeutic agent is selected from the group consisting of
   scyllo-inositol, a scyllo inositol derivative selected from the group consisting of amino-scyllo-inositol, fluoro-scyllo-inositol, deoxy-scyllo-inositol keto-scyllo-inositol and sulf-oscyllo-inositol; salts thereof and mixtures thereof; and mixtures thereof with an inositol stereoisomer selected from the group consisting of myo-inositol, epi-inositol, cis-inositol, allo-inositol, neo-inositol, chiro-inositol, muco-inositol, dextro-inositol levo-inositol, mixtures thereof and salts thereof.

33. The method of claim 32, wherein the scyllo-inositol is administered in an amount of about 200 to about 800 mg/kg/day.

34. The method of claim 33, wherein the scyllo-inositol is administered in an amount of about 250 mg/kg/day to about 600 mg/kg/day.

35. The method of claim 34, wherein the scyllo-inositol is administered in an amount of about 300 to about 400 mg/kg/day.

36. The method of claim 24, wherein the mammal is a transplant subject.

37. The method of claim 24, wherein the mammal is afflicted with an auto-immune disease.

38. The method of claim 24, further comprising administering to the mammal other immuno-suppressant therapy.

39. The method of claim 1, wherein the amount of the therapeutic agent administered is effective to enhance, inhibit or suppress the proliferation and/or differentiation of T lymphocytes into lymphocytes selected from the group consisting of helper T lymphocytes, cytotoxic killer T lymphocytes and suppressor T lymphocytes.

40. The method of claim 1, wherein the therapeutic agent is administered as a composition further comprising a biologically acceptable carrier.

41. The method of claim 40, wherein the biologically acceptable carrier comprises a pharmaceutically acceptable carrier.

42. The method of claim 41, wherein the therapeutic agent is selected from the group consisting of myo-inositol, a myo-inositol derivative selected from the group consisting of amino-inositol, fluoro-inositol, deoxy-inositol, keto-inositol and sulfo-inositol, mixtures thereof and salts thereof.

43. The method of claim 41, wherein the therapeutic agent is selected from the group consisting of chiro-inositol, a chiro-inositol derivative selected from the group consisting of amino-chiro-inositol, fluoro-chiro-inositol, deoxy-chiro-inositol, keto-chiro-inositol and sulfo-chiro-inositol, mixtures thereof and salts thereof.

44. The method of claim 41, wherein the therapeutic agent is selected from the group consisting of scyllo-inositol, a scyllo-inositol derivative selected from the group consisting of amino-inositol, fluoro-inositol, deoxy-inositol, keto-inositol and sulfo-inositol, mixtures thereof and salts thereof.

45. The method of claim 40, wherein the composition is administered in solid form.

46. The method of claim 40, wherein the composition is administered orally.

47. The method of claim 40, wherein the composition is administered topically.

48. The method of claim 47, wherein the topical composition is an aqueous or non-aqueous solution, oil-in-water or water-in-oil suspension, cream, gel or lotion.

49. The method of claim 40, wherein the composition is administered by means of an implant.

50. The method of claim 40, wherein the composition is administered by transdermal delivery.

51. The method of claim 50, wherein the transdermal composition is administered by iontophoretic delivery.

52. The method of claim 40, wherein the composition is administered in the form of a slow release formulation.

53. The method of claim 46, wherein the orally administered composition comprises a solution, suspension or emulsion.

54. The method of claim 40, wherein the composition is administered by injection.

55. The method of claim 40, wherein the composition is administered in vaporizable form.

56. The method of claim 40, wherein the composition is administered from a skin patch.

* * * * *

UNITED STATES PATENT AND TRADEMARK OFFICE
CERTIFICATE OF CORRECTION

Figure 1B:
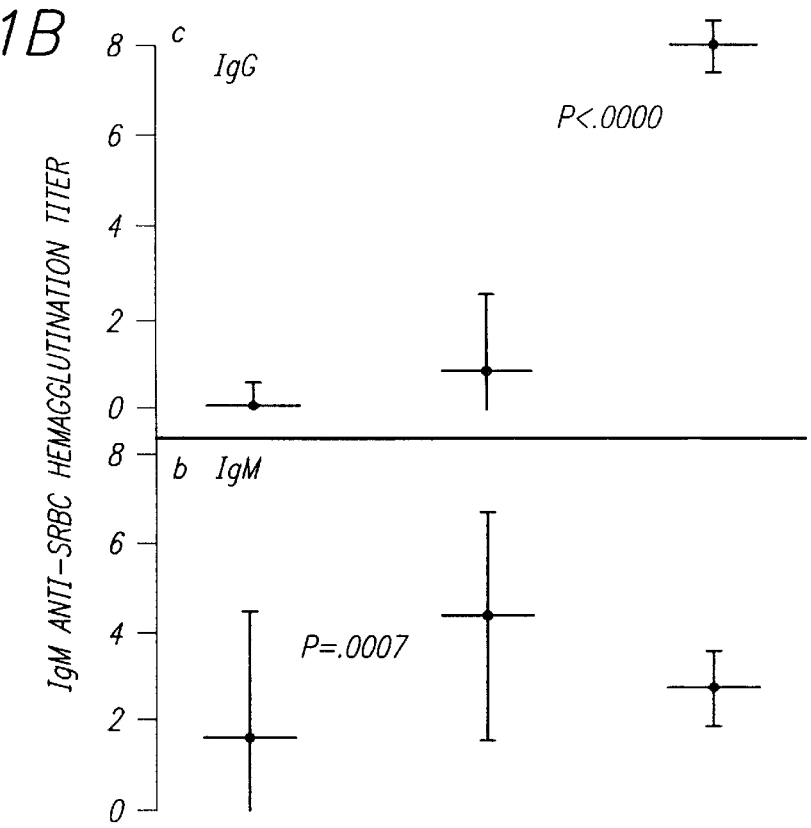
FIG. 1(b) shows a primary antibody response (IgM) to SRBC by immunodeficient XID mice fed the control diet (left column, ●) or the same diet supplemented with 0.4% (w/w) myo-inositol (middle column, ○) and immunocompetent mice fed the control diet (right column, X)

PATENT NO. : 5,998,485
DATED : Dec. 7, 1999
INVENTOR(S) : Marvin L. Tyan and Dolly B. Tyan It is certified that error appears in the above-identified patent and that said Letters Patent is hereby corrected as shown below:

Column 2, line 23, delete "FIG. 1*(a)*" and insert therefor--Figure 1A--.
Column 2, line 29, delete "FIG. 1*(b)*" and insert therefor --Figure 1B(b)--.
Column 2, line 34, delete "FIG. 1(c)" and insert therefor --Figure 1B(c)--.
Column 14, line 53, delete "FIG. 1" and insert therefor --Figure 1A and Figure 1B--.
Column 15, line 46, delete "stercoisomers" and insert therefor --stereoisomers--.
Column 15, line 51, delete "1.600" and insert therefor --1,600--.
Column 15, line 63, delete "keto inositol and" and insert therefor --keto-inositol, and--.
Column 16, line 7, delete "sulfo-scyllo-iniositol" and insert therefor --sulfo-scyllo-inositol--.
Column 16, lines 16-17, delete " stercoisomer derivatives" and insert therefor --stereoisomer derivatives--.
Column 16, line 32, delete "-" from the word "lymphocyte".
Column 16, line 42, delete "sulfozinositol" and insert therefor --sulfo-inositol--.
Column 17, line 41, insert --,-- after "amino-scyllo-inositol".
Column 17, line 57, insert --,-- after "deoxy-scyllo-inositol".
Column 17, line 58, delete "sulf-oscyllo-inositol;" and insert therefor --sulfo-scyllo-inositol;--.
Column 17, line 63, delete "inositol levo-inositol" and insert therefor --inositol, levo-inositol--.

Signed and Sealed this

Twelfth Day of December, 2000

*Attest:*

Q. TODD DICKINSON

*Attesting Officer*   *Director of Patents and Trademarks*